United States Patent [19]

Agee

[11] 4,349,922
[45] Sep. 21, 1982

[54] JOINT PROSTHESIS WITH IMPROVED ARTICULATION MEANS

[76] Inventor: John M. Agee, 3980 Bartley Dr., Sacramento, Calif. 95822

[21] Appl. No.: 246,834

[22] Filed: Mar. 23, 1981

Related U.S. Application Data

[63] Continuation-in-part of Ser. No. 14,391, Feb. 22, 1979, abandoned.

[51] Int. Cl.³ .............................................. A61F 1/03
[52] U.S. Cl. ..................................... 3/1.91; 128/92 C
[58] Field of Search ............................. 3/1.91, 1.911; 128/92 C

[56] References Cited

U.S. PATENT DOCUMENTS

| | | | |
|---|---|---|---|
| 3,651,521 | 3/1972 | Devas | 3/1.91 |
| 3,760,427 | 9/1973 | Schultz | 3/1.91 |
| 3,869,729 | 3/1975 | Attenborough | 3/1.91 |
| 3,889,300 | 6/1975 | Smith | 3/1.91 |
| 4,040,131 | 8/1977 | Gristina | 3/1.91 |
| 4,100,626 | 7/1978 | White | 3/1.91 |
| 4,183,104 | 1/1980 | Frey | 3/1.91 |
| 4,206,517 | 6/1980 | Pappas et al. | 3/1.91 |

*Primary Examiner*—Clifford D. Crowder
*Attorney, Agent, or Firm*—John L. McGannon

[57] ABSTRACT

A prosthesis for a joint of the human body, such as the metacarpophalangeal, knee, or other joint. The prosthesis includes at least a pair of elongated stem members adapted to be inserted into and bonded to two bones which met to form the joint. The adjacent surfaces of the two stem members form an interface with each other to present the prosthetic joint interface. The two members are interconnected by a pivot mechanism comprised of a rotatable element in a slot in a first of the stem members, and a linking pin pivotally coupled to the element and to the second stem member so that the second stem member can pivot relative to the first stem member about three different axes. The mechanism is made so that the pivotal movement of the second stem member relative to the first stem member about any one of the axes can be accomplished without imparting significant torsional or bending loads to the first stem member. This assures that the first and second stem members remain implanted in the respective bones at all times.

40 Claims, 25 Drawing Figures

JOINT PROSTHESIS WITH IMPROVED ARTICULATION MEANS

This is a continuation-in-part of application Ser. No. 14,391, filed Feb. 22, 1979, now abandoned.

BACKGROUND OF THE INVENTION

Prosthetic devices adapted to be used at a metacarpophalangeal joint (hereinafter MP joint) of a human hand are of two general types, namely, those which act as spacers to facilitate biologic reconstruction of a joint out of fibrous (scar) tissue, and those of more rigid mechanical design which attempt to reconstruct one or several of the axes of motion of the normal MP joint. The former type, illustrated by the Silastic (a registered trademark of DOW Chemical Company for silicone rubber) rubber design of Swanson (hereinafter described), in general, does not place undue stress on the bone and soft tissues into which it is implanted. The latter type, illustrated by the Steffee and Flatt designs (hereinafter described) are constructed of metal-plastic or metal structures, respectively, are in general prosthetic articulations which are constrained at the junctions of their metacarpal and phalangeal parts in such a manner that they transfer torsional and/or bending loads from one part to the other. This results in the parts becoming essentially rigidly coupled together, thereby resulting in mechanical (fatigue) failure of either the prosthesis itself or the biologic tissue, i.e., bone, into which the prosthesis is implanted. In addition, none of the prostheses currently in use substantially reconstruct the biomechanical mechanisms through which the normal MP joint moves and dynamically stabilizes itself.

Prosthetic devices for the metacarpophalangeal joint have been devised by a number of individuals including Flatt, Swanson, Niebauer, Steffee and Walker. A discussion of the Flatt prosthetic device is found in a textbook entitled, "The Care of the Rheumatoid Hand," by Adrian E. Flatt (C.V. Mosby Company, St. Louis 1974) pp 160–166. Flatt's device includes two elongated members for insertion in two adjacent bones of a joint, the members being connected by a single hinge allowing only one degree of freedom of the prosthetic joint. Experience with the Flatt prosthesis has demonstrated either mechanical failure of the prosthesis itself or of the metacarpal and phalangeal bones into which its stems are inserted.

The Swanson device is discussed in a text entitled, "Flexible Implant Resection Arthroplasty in the Hand and Extremities," by Alfred B. Swanson (C.V. Mosby Company, St. Louis 1973) Chapter 8, pp. 147–159. This device comprises a one-piece member of silicone rubber which allows movement of one bone with respect to the other with multiple degrees of freedom. The flexible implant serves to align the skeletal elements while allowing mechanical motion to occur. Biologic encapsulation together with the structural nature of the implant itself serve to reconstruct motion at the level of the resected joint. In the Swanson design, no discrete axis of motion is reconstructed. Shearing forces and bending moments are imparted to the prosthesis itself resulting in eventual (fatigue) failure of a significant number of the implants.

The Neibauer device is similar in construction to that of the Swanson device except that the silicone rubber is integral with a fabric belt in the midportion of this one-piece member prosthesis. The narrow midportion junction of the Neibauer prosthesis forms a hinge which reconstructs the flexion-extension axis of the joint. Unlike the smooth surfaced Swanson design, the Neibauer design has a fabric weave integral with the surface of the stem portions of the same which facilitates a mechanical bond of the prosthesis to the intramedullary cavities of the adjacent bones.

The Steffee design is disclosed by U.S. Pat. No. 3,506,982. This device effectively reconstructs the flexor and extensor moment arms at the level of the MP joint but its mechanical features transfer torsion and bending loads between stem members resulting in either mechanical failure of the prosthesis itself or of its mechanical junction with the adjacent metacarpal and phalangeal bones in a significant number of clinical cases.

The Walker design is disclosed in a text entitled, "Human Joints and Their Replacements", by Peter S. Walker (Charles E. Thomas, Publishers, Springfield, Ill. 1977). The Walker device comprises a plastic metacarpal stem, metal phalangeal stem, and a snap-in plastic axle. The stems have a circular section, with knurling to attach at all points to the cement. The plastic head is part of a sphere, and has a dorsal-volar slot to accommodate the metal post. An elongated hole through the side of the plastic head, and a circular hole in the metal post, accommodate the axle. The back of the collar of the phalangeal component is flat to locate against the bone, while at the front, the surface is part of a sphere, of only slightly larger radius of curvature than the plastic head. When the joint is assembled, load-bearing occurs between the spherical surfaces and not on the axle. At 0° of flexion, radial-ulnar motion is allowed, but progressively with flexion, this lateral motion decreases because the axle is now restrained.

Because of the drawbacks of the prosthetic devices of the type described, a need has continued for an improved prosthesis which allows for movement of one bone adjacent to a joint relative to a second bone adjacent to the joint without transfer by the stems of the prosthesis of excessive torsion and bending loads to the second bone. By minimizing these loads, there will be substantially no breaking of the bond between the stem members of the device and the bones or the device itself. In addition, the need also exists for an improved prosthetic design to reconstruct the axes about which the normal MP joint moves. None of the currently available prostheses reconstructs the longitudinal rotational axis of the finger as determined by the biomechanics of the normal MP joint.

SUMMARY OF THE INVENTION

The present invention satisfies the aforesaid need by providing a prosthetic device of improved design which allows one of a pair of relatively shiftable elongated stem members of the device to move relative to the other stem member in three degrees of freedom without transferring any substantial torsional and bending loads to the other member. The foregoing advantages can be realized even though the device can be used in a number of different joints of the body to carry out the functions of the normal joints which must be replaced because of rheumatoid arthritis and other arthritities associated with the joint.

To this end, the present invention includes a rotatable element coupled to one of the stem members and a linking pin pivotally connecting the element with the second stem member. The axis of rotation of the element with respect to the first stem member provides a first degree of freedom and the axes provided by the elongated parts of the linking pin provide second and third degrees of freedom, all of which assure alignment and apposition of the prosthetic articular surfaces throughout a substantially normal range of joint motion of the first member relative to the second member without causing a bending action or a transfer of torsional and bending loads between the stem members. This feature is particularly important in functional hand activities in which externally applied forces deviate a finger to either the radial or ulnar side of the hand or force the finger to rotate in a torsional manner, each of which forces should be substantially absorbed, controlled and/or dissipated by the ligamentous and musculotendinous soft tissues that have been reconstructed during joint implantation. The linkage mechanism thereof ensures proper alignment and apposition of the prosthetic articular surfaces essential for transfer of the joint reaction force permitting restricted motion of the first member relative to the second member without causing a bending action or a transfer of substantial torsional and bending loads between the stem members. The device, especially the linkage mechanism thereof, is suitable for implantation in the metacarpolphalangeal, knee and wrist joints and can be adapted for use in joints at other parts of the human body.

The primary object of this invention is to provide a prosthetic device of improved construction which can be inserted at a joint of the human body in a manner such that the bone at one side of the joint can pivot relative to the bone on the opposite side of the joint without transferring any substantial torsional and bending loads to the bone at the other side of the joint, thereby assuring the continued implantation of the device and avoidance of mechanical failure of the device or mechanical breakdown of the bond between the device and the skeletal system.

Other objects of this invention will become apparent as the following specification progresses, reference being had to the accompanying drawing for an embodiment of the invention.

IN THE DRAWING

FIG. 2 is a top plan view of the prosthesis on a reduced scale from that of FIG. 1;

FIG. 3 is a bottom plan view of the prosthesis on the scale of that shown in FIG. 2;

FIG. 4 is an end elevational view of a part of the metacarpal head portion of the prosthesis looking in the direction of the metacarpal base or wrist;

FIG. 4a is a side elevational view of the pivot mechanism of the prosthesis;

FIG. 4b is an end elevational view of the rotatable element forming a part of the pivot mechanism of FIG. 4a;

FIG. 4c is another end elevational view of the rotational element looking from the distal end of the pivot mechanism;

FIG. 12 is a front elevational view of another embodiment of the disk forming a part of the pivot mechanism shown in FIG. 4a;

FIG. 14 is a view similar to FIG. 1 but showing a second embodiment of the pin forming a part of the pivot mechanism as shown in FIG. 4a;

The prosthesis of the present invention is broadly denoted by the numeral 10 and is illustrated in detail in FIGS. 1-4 with respect to its use in the metacarpophalangeal joint (hereinafter MP joint) of a thumb or a finger of the human hand. While the prosthesis of the invention, as illustrated (FIGS. 1-10), is suitable for this particular joint, the structural details of the prosthesis, including the unique pivot mechanism thereof, are suitable for use with the knee, elbow, wrist and other body joints as well. In all cases, the prosthesis of the invention is operable to align the skeletal members at a prosthetic joint interface by means of a mechanism that allows the dissipation of torsional loads and bending moments at the level of the joint interface. By doing this, the prosthesis of the present invention avoids the problems of prosthetic joint failure due either to loosening of the prosthesis at its interface with the bone or to mechanical failure of the prosthetic joint itself, both of which are a direct result of transmission of excessive torsional loading and bending moments across the prosthetic articulation.

Figure 1:
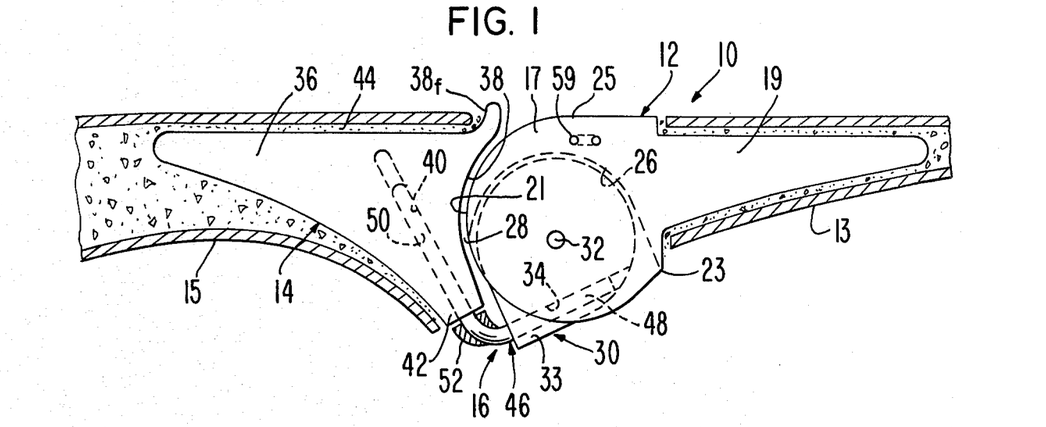
FIG. 1 is a side elevational view of the prosthesis of the present invention for use with the metacarpophalangeal joint of the human hand, the bones of the joint being shown in cross section.

Prosthesis 10 includes a first, elongated member 12 adapted to be coupled with the metacarpal bone 13 of a thumb or finger of the hand, and a second member 14 adapted to be coupled to the proximal phalanx 15 of the finger. The first and second members are coupled together by a pivot mechanism 16 to allow movement of member 14 relative to member 12 in three degrees of freedom which substantially simulate the three degrees of freedom in which the proximal phalanx of a normal finger moves relative to the metacarpal bone 13.

Member 12 has a head 17 integral with a stem 19. The shape of the stem is pointed so that it can be inserted into the hollow or medulla of metacarpal bone 13. The stem is bonded in the medullary canal by a currently appropriate clinical technique. In the current state of the art, this would require cementing (grouting) the stem in the medullary canal by polymethyl methacrylate or by allowing tissue ingrowth into a porous surface of the stem of the prosthesis to thereby interconnect the stem and the metacarpal bone 13. Head 17 simulates the metacarpal head at the MP joint of a normal finger. The outer surface 21 of the head is substantially spherical and extends typically from a location 23 forwardly and upwardly to a location 25 near the top flat surface of member 12. Head 21 has a slot 26 which is open at surface 21 and extends from a location near location 23 to a location identified by the numeral 28 (FIG. 1). The slot 26 is adapted to receive a rotatable element 30 forming one part of pivot mechanism 16, the element being rotatably mounted on head 17 by a pin 32 carried on head 17 at each side of slot 26 so that the element rotates in slot 26 about the axis of pin 32. Element 30 is shown as being disk-like in construction, but it can be of any other suitable shape, if desired.

Figures 2, 3, 4, 4A, 4B, 4C:
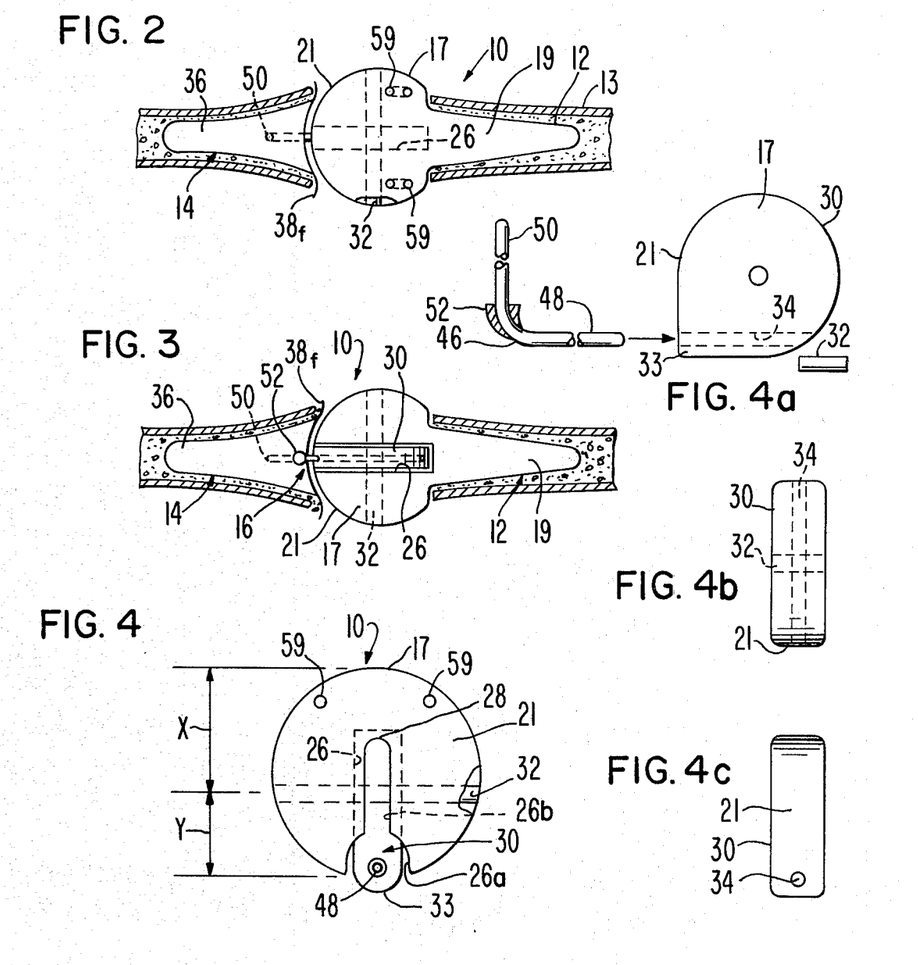

The continuation of slot 26 onto surface 21 of head 17 is widest in its volar extent to accommodate for element 33 and is denoted by the numeral 26a in FIG. 4. The dorsal extension of slot 26 narrows to accomodate pin 46 (hereinafter described) forming pivot mechanism 16 to permit a forced hyperextension of the joint. This dorsal extension of slot portion 26a is denoted by the numeral 26b in FIG. 4. This feature allows hyperextension of the joint without causing a constraint on the same that might transmit undue loads on the bone-cement interface on one side of the joint to the bone-cement interface on the opposite side of the joint or undue stress on the prosthesis itself.

While the shape of prosthetic metacarpal head 17 is stated as being substantially spherical, it is at least partially spherical on its articular surface 21 but essentially it is anatomically the same as the shape of the normal metacarpal head with a portion of its attached collateral ligaments, a shape modified primarily to accommodate for the needs of a mechanical linkage as opposed to a biologic linkage. In the case of the MP joints of the fingers, this shape is most nearly spherical for the ring finger MP joint, with moderate assymetry of the radial and ulnar sides of the metacarpal head in the case of the long and little fingers, and marked assymetry of the same sides with respect to the index metacarpal head. This shape allows element 30 to have a projecting part 33 to extend outwardly from surface 21 as shown in FIGS. 1 and 4a. Part 30 is provided with a bore 34 therein for receiving a part of pin 46.

On each of the dorso-radial and dorso-ulnar aspects of metacarpal head 17 are provided a pair of open end passages 59 for receiving surgical suture material to re-suspend the collateral ligaments during reconstruction of the soft tissues. These passages 59 are shown in FIGS. 1, 2, 4 and 10c.

Member 14 has a stem 36 which is pointed to facilitate its insertion into the hollow or medullary canal of the proximal phalanx 15. The margin of surface 38 of member 14 is elevated into a flange 38f (FIGS. 1–3) to prevent migration of member 14 into the proximal end of phalangeal bone 15. The stem is cemented in place with a suitable bonding mechanism as described above with reference to stem 19 of member 12. Member 14 has a surface 38 which is adjacent to and substantially complemental with, and normally engaging surface 21 of head 17. Also, surface 38 is essentially similar in shape to the proximal articular surface of a normal proximal phalanx. Also member 14 has a bore 40 which extends from the volar part 42 to a location near but spaced from the dorsal surface 44 thereof at an angle relative to the longitudinal axis of member 14 as shown in FIG. 1. This bore is adapted to receive the above-mentioned pin of pivot mechanism 16 and one reason for the angularity of bore 40 is to space the bore a considerable distance away from surface 38 to provide sufficient structural strength for member 14 when it is mounted on the pin.

Pivot mechanism 16 further includes a generally L-shaped pin 46 having a first part 48 rotatably and slidably received within bore 34 and a second part 50 rotatably and slidably received within bore 40. The upper end of pin part 50 bears against or is slightly spaced from the open top of bore 40 as shown in FIG. 1. Also, pin 46 has a shoulder 52 near the junction of parts 48 and 50, the shoulder presenting a bearing surface for engaging the lower face of the volar part 42 of member 14. For purposes of illustration, the bearing surface of shoulder 52 is flat but it could be of another shape, if desired. This limits the downward movement of member 14 on pin 46 and facilitates rotation of member 14 relative to pin 46.

By virtue of pivot mechanism 16 defined by pin 46, pin 32 and element 30, member 14 is movable about three degrees of freedom relative to member 12 while keeping the attached skeletal elements, namely metacarpal bone 13 and proximal phalanx 15, properly aligned at their prosthetic joint interfaces in a system that dissipates torsional loading and bending moments while preventing volar, radial or ulnar subluxation of the proximal phalanx with respect to the metacarpal and simultaneously reconstructing the moment arms for the flexor tendons (flexor digitorum sublimus and profundus), the tendons of the intrinsic muscles and the entire extensor tendon mechanism at the level of the MP joint. These three degrees of freedom are rotation of member 14 about the longitudinal axis of pin 32, rotation of member 14 about the longitudinal axis of part 48 of pin 46, and rotation of member 14 about the longitudinal axis of part 50 of pin 46. In the case of deviation of the finger, i.e., movement in the radial or ulnar direction, there could be rotation of member 14 about the longitudinal axis of part 50 of pin 46 as well as the concomitant extraction of a portion of pin part 48 from bore 34 while keeping the proper alignment between metacarpal bone 13 and proximal phalanx 15 as appreciated at their prosthetic articular surfaces 21 and 38, respectively. Also, part 48 of pin 46 reconstructs the moment arm system for rotational (torsional) stability of the finger.

Figure 10A:
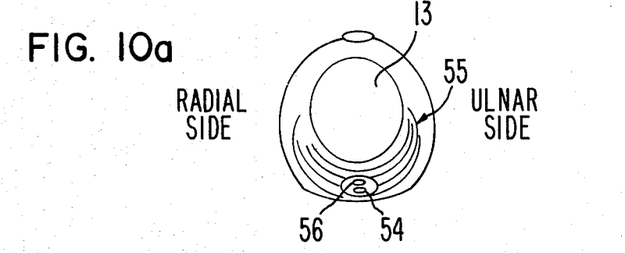
FIG. 10a is an end elevational view of a part of the metacarpal head of a normal MP joint showing the extensor and flexor tendon mechanisms and the collateral ligaments looking in the direction of the metacarpal base or wrist.
Figure 10B:
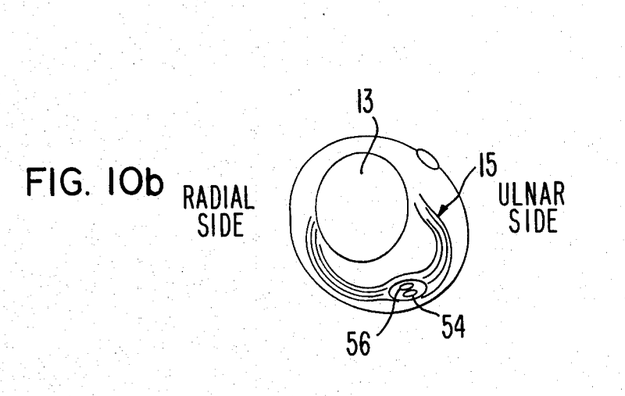
FIG. 10b is a view similar to FIG. 10a but showing the attenuation of the ligaments that stabilize the flexor and extensor mechanisms.
Figure 10C:
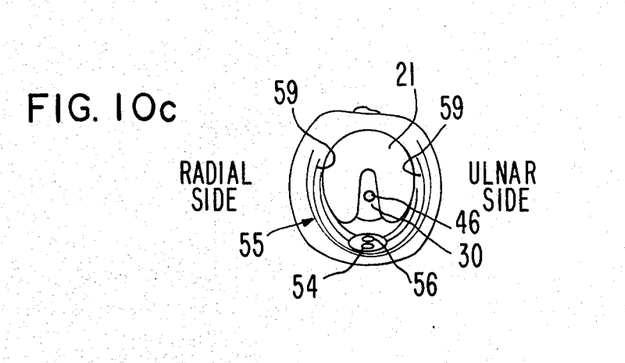
FIG. 10c is a view similar to FIGS. 10a and 10b but showing a part of the prosthetic metacarpal head of this invention and illustrating its use in reconstructing the flexor and extensor tendon mechanisms and their associated collateral ligaments.

In use, the diseased MP joint of the hand is approached through a dorsal skin incision entering the joint by dividing the transverse lamina of the extensor hood mechanism by techniques common to the art of surgical reconstruction of this joint. The joint capsule is incised and the metacarpal head is resected at its proximal extent near or at the junction of the metaphyseal flare. Appropriate intramedullary remurs are used to remove the cancellous bone from the intramedullary canal of the metacarpal bone 13. The proximal articular surface of the proximal phalanx is then perforated to facilitate reaming of the medullary canal of the proximal phalanx. A prosthesis is selected appropriate to size and shape for the particular MP joint being replaced. Reaming is continued until stems 19 and 36 can be appropriately accommodated, following which each of such stems are installed in the proper medulla with pin 46 inserted into bores 34 and 40, respectively, to link members 12 and 14 of prosthesis 10. Once the degree of bone resection and skeletal realignment is considered to be adequate, the metacarpal and phalangeal portions are removed and later cemented in place. The remains of the collateral ligaments are advanced dorsally thereby resuspending the flexor tendon mechanism beneath the prosthetic metacarpal head. The dorsal end of the collateral ligaments are then secured to the dorso-ulnar and dorso-radial aspects of the prosthetic metacarpal head 12 using surgical sutures placed into the same and through the open end passages 59 as depicted in FIG. 10c. Scar tissue will eventually encapsulate the various parts of the prosthesis, yet member 14 can continue to move with respect to member 12 about the three degrees of freedom mentioned above.

Figure 5:
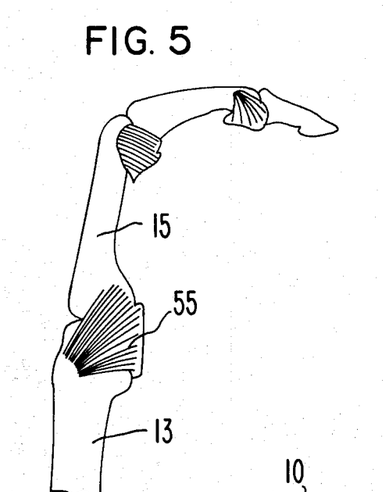
FIG. 5 is a side elevational view of the bones of a finger showing the metacarpophalangeal joint and the collateral ligaments at such joint.
Figure 6:
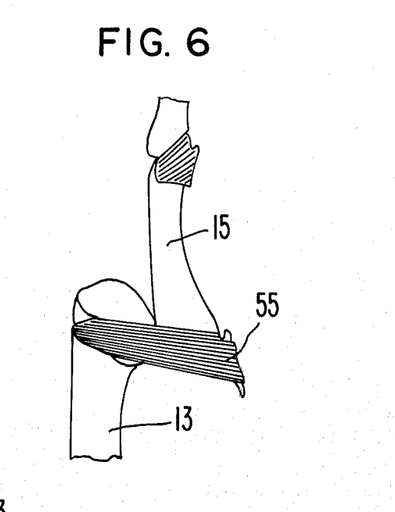
FIG. 6 is a view depicting volar dislocation of the proximal phalanx with respect to the metacarpal head with an associated complete tear of the collateral ligaments.
Figure 7:
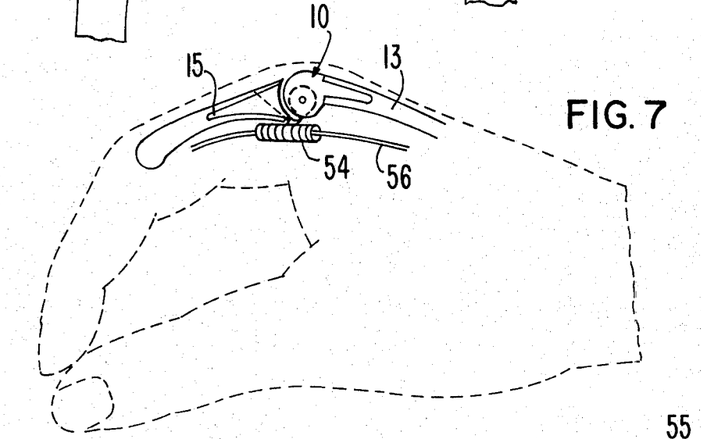
FIG. 7 is a side elevational view of the right hand of a human, showing the prosthesis in place for the index finger.

Pivot mechanism 16 of prosthesis 10 serves a number of functions. It replaces the function of the collateral ligaments which are typically attenuated or destroyed in rheumatoid arthritis and/or other arthritities of the MP joint. In such a clinical situation, there is a volar subluxation or dislocation of the base of the proximal phalanx with respect to the metacarpal head. This is illustrated in FIGS. 5 and 6 in which FIG. 5 shows a normal finger and FIG. 6 shows the condition known as volar dislocation. In FIG. 5, the collateral ligaments properly align metacarpal bone 13 with proximal phalanx 15. The anatomical dispositon of the fibers of the collateral ligaments prevents volar subluxation of the base of the proximal phalanx on the metacarpal head by virtue of their oblique course from the dorsal aspect of the metacarpal head to the volar base of the proximal phalanx. This is most important in opposing the dislocating forces of the flexor digitorum profundus and the flexor digitorum sublimus tendons together with the forces of the intrinsic muscles of the hand.

Figure 8:
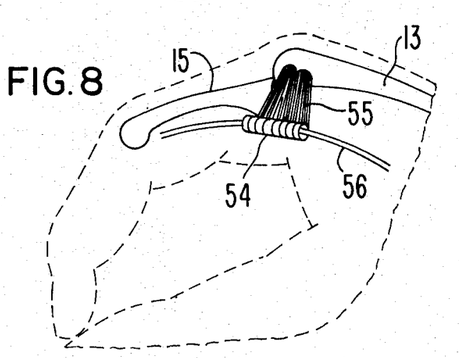
FIGS. 8 and 9 are views similar to FIG. 7 but showing a volar subluxation condition and a normal condition, respectively, of the metacarpolphalangeal joint.
Figure 9:
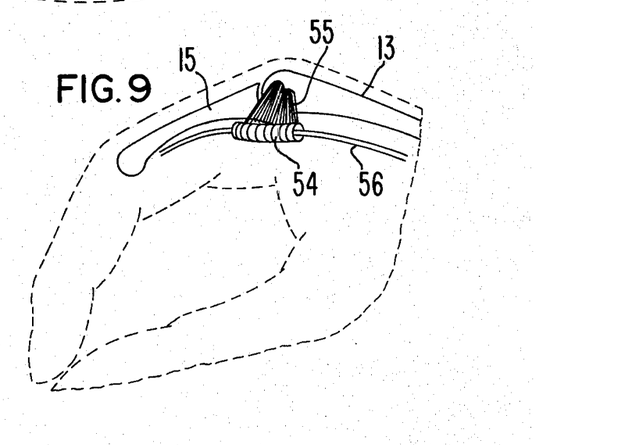

The glenoidal portion of the collateral ligaments 55 is responsible for suspending the flexor tendon pulley or tunnel 54 (FIGS. 9 and 10a) appropriately in a normal finger immediately beneath the volar aspect of the MP joint thereby assuring the proper moment arm for the flexor tendons at the level of the MP joint. In FIGS. 8 and 10b, a progressive degree of attenuation of the two portions of the collateral ligaments on either side of the MP joint result in progressive degrees of subluxation of the base of proximal phalanx 15 on the metacarpal head leading to joint subluxation of the same as shown in FIG. 8. FIG. 6 shows advanced attenuation of the ligaments with secondary dislocation of proximal phalanx 15 with respect to metacarpal 13. Progressive degrees of subluxation corresponding to lesser amounts of MP joint collateral ligament attenuation can exist. Each increment of volar subluxation of the base of the proximal phalanx on the metacarpal head results in a concomitant increase in the mechanical advantage of the flexor tendons 56 (FIGS. 7-9 and 10b) to flex the MP joint due to a progressive increase in the distance between the axis of flexion and extension of the MP joint and the powerful flexor tendons 56. This increased mechanical advantage is shown in FIG. 8 in which a condition of volar subluxation is shown although not to the extent of that shown in FIG. 6.

When properly installed at the interface between metacarpal bone 13 and proximal phalanx 15, prosthesis 10 returns toward normal the moment arms of the flexor and extensor tendons with respect to the biomechanical instant center of the MP joint for flexion and extension as reconstructed by prosthesis 10. In the design of prosthesis 10, the proper balance between flexor and extensor forces acting on the implanted prosthesis is defined by two interdependent mechanical factors:

1. The gliding motion of articular surface 38 of member 14 on the semispherical articular surface 21 of member 12 which defines a flexion-extension axis slightly dorsal to pin 32.
2. The mechanical suspension of pivot mechanism 16 by pin 32 which resists the volar subluxing forces of the flexor tendons and intrinsic muscles as it reconstructs the function of the collateral ligaments thereby preventing volar subluxation of the base of the proximal phalanx with respect to the metacarpal head.

By adjusting the semispherical shape of the prosthetic metacarpal head 25 together with the position of pin 32, a balance of the flexor and extensor forces can be achieved. The dorso-volar position of axis 32 is depicted by distances x and y in FIG. 4. This need for balancing the flexor and extensor forces at MP joint level is a recognized mechanical need of a prosthetic joint and is extremely important to the design of a prosthesis for the MP joint.

In the design of prosthesis 10 for use in the metacarpophalangeal joint of the human hand, element 30 is shorter in vertical height (from the dorsal aspect to the volar aspect of head 17 as seen in FIG. 4) such that the lower part or aspect of element 30 aligns with the lower end of head 17, the upper end of element 30 being spaced below the dorsal extent of head 17, thereby positioning the flexion-extension axis (pin 32) more than 50% (perhaps 60% to 70%) of the way from the dorsal to the volar side of the prosthesis while assuring a smooth dorsal and distal aspect of metacarpal head 17 for the extensor tendon and its intimately associated extensor hood mechanism to glide upon.

A typically progressive volar subluxation of the proximal phalanx on the metacarpal head is accompanied by progressive degrees of dislocation of the extensor tendon from the dorsal aspect of the metacarpal head to the ulnar side of the MP joint. This results in a progressive decrease in the moment arm of the extensor tendon and of its ability to extend the MP joint and balance the flexor forces generated by the progressively more mechanically advantaged flexor tendons. Also, the progressive attenuation of the collateral ligaments typically allows the flexor and extensor tendons to "bow string" across the ulnar aspect of the MP joint, as depicted in FIG. 10b thereby producing an ulnar deviating force on the proximal phalanx with respect to the metacarpal head. This patho-mechanical mechanism is responsible for the progressive ulnar drift in the fingers in rheumatoid arthritis of the MP joint. Pivot mechanism 16, when properly linking members 12 and 14, not only realigns the base of the proximal phalanx with metacarpal head 17 to reconstruct the moment arms of the extensor and flexor tendons, but together with surgical soft tissue reconstruction, it also realigns the flexor and extensor tendons with respect to their pathologically altered moment arms as shown in FIG. 10c for ulnar deviation of the proximal phalanx at the MP joint. This is achieved notwithstanding the degree of deterioration of the collateral ligaments.

Pivot mechanism 16 also reconstructs the longitudinal rotational axis of the finger at the level of the MP joint. As shown in FIGS. 9 and 10a, the normal MP joint has flexor tendons 56 contained in pulley tunnel 54 which extends longitudinally under and adjacent to the volar aspect of the MP joint. Flexor tendons 56 and tunnel 54 define the longitudinal rotational axis of the MP joint in progressive degrees of flexion of the same as when the tip of the finger is in contact with the distal end of the thumb.

During functional use of the finger, flexor tendons 56 are under marked tension and are contained tightly in tunnel 54. This pulley tunnel, which extends from the proximal extent of head 17 to the volar aspect of proximal phalanx 15 distally constitutes a longitudinal bearing for flexor tendons 56 which are under tension and thereby jointly define the longitudinal rotational axis of the finger at the level of the MP joint which is in any of a number of degrees of flexion. When the MP joint is extended, the collateral ligaments are relatively relaxed, thereby allowing the base of the proximal phalanx to migrate to the radial or ulnar side of the metacarpal head without obligating itself to a significant degree of longitudinal rotation. This varies with the joint and the particular patient. With progressive degrees of flexion, from about 30° to 90°, the cam-like effect of the metacarpal head makes the collateral ligaments tighten, thereby snugly securing the fibro-cartilagenous portion of tunnel 54 just volar to the metacarpal head, obligating the base of the proximal phalanx and thereby the entire finger to rotate about the dorsal aspect of tendons 56 and their tunnel 54.

A significant aspect of this issue is that the same pathological process which attenuates the collateral ligaments, thereby permitting progressive degrees of volar subluxation of the base of the proximal phalanx, also destroys the ability of the proximal portion of tunnel 54 to act as a bearing for the rotational axis of the finger. Each of the intrinsic muscles, i.e., the interossei and lumbricals, and the extensor tendons, together with the entire extensor hood mechanism, have moment arms that relate to this longitudinal rotational axis of the finger. The dorsal to volar depth (x plus y of FIG. 4) of the MP joint is the moment arm about which the extensor tendon and the entire extensor hood mechanism acts to achieve rotational stability of the finger. The extensor tendon acts on the dorsal and proximal extents of the extensor hood mechanism, thereby rotating a typical index finger into supination by virtue of forces transmitted in a circular fashion about the MP joint through the extensor hood mechanism. Similar forces are derived from the extensor tendon mechanism to the long, ring and little fingers by virtue of the varying angles of approach of the junctura tendons.

Pivot mechanism 16, while functioning to prevent volar subluxation of the proximal phalanx on the metacarpal head, also assures that the intrinsic muscles of the hand will be provided with the proper moment arms for radial-ulnar deviation of the finger about an anterior/posterior axis. In the normal finger MP joint in the extended position, this radial-ulnar deviation occurs about an axis passing through the metacarpal head. Progressive degrees of joint flexion in the normal joint results in elimination of radial and ulnar displacement of the distal end of the finger as the intrinsic interosseous muscles change from a function of radial-ulnar deviation to a function of rotation of the entire finger. Because they are rotators of the finger, the interossei also acting on a flexed MP joint are torsional stabilizers of the finger. Most importantly, pivot mechanism 16 jointly provides for the proper moment arms of the intrinsic muscles to radially and ulnarally deviate the extended finger or rotate or torsionally stabilize the flexed finger. Both of these motions occur about vertical part 50 of pin 46, it being noted that radial or ulnar deviation of member 14 not accompanied by rotation of part 14 results in extraction of part 48 of pin 46 from bore 34.

When prosthesis 10 is in place, part 48 of pin 46 will be generally at an angle of 30° to 35° with reference to the longitudinal axis of proximal phalanx 15 when the latter is extended as shown in FIG. 1. This allows part 50 of pin 46 to be at an angle of about 60° to the longitudinal axis of proximal phalanx 15.

Figure 9A:
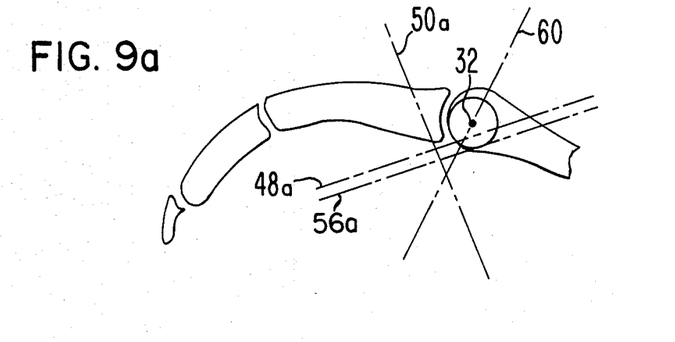
FIG. 9a is a schematic view of the bones of a finger, showing the axes of movement of the finger when the prosthesis is in place.

The three degrees of freedom provided by prosthesis 10 for a finger relative to the MP joint can be illustrated with reference to the finger shown in FIG. 9a. In this figure, the finger can have flexion-extension movement about a first axis (pin 32) perpendicular to the figure. A second degree of freedom is provided by the movement of the finger about the longitudinal axis 48a of part 48 of pin 46, i.e., the longitudinal rotation of the finger relative to the joint. Axis 48a is essentially parallel to the rotation axis 56a of the normal finger, axis 56a normally passing obliquely through tunnel 54 and flexor tendons 56 of the normal finger. A third degree of freedom is provided by the radial-ulnar movement of the finger about the longitudinal axis 50a of part 50 of pin 46, axis 50a being angularly disposed relative to shaft 32 and part 48. Axis 50a is spaced from the axis 60 (FIG. 9a) about which radial-ulnar deviation of the normal finger occurs.

Most importantly, pivot mechanism 16 of prosthesis 10 provides the foregoing degrees of freedom and the foregoing functions while dissipating torsional loading of the joint surface and dissipating bending moments at the level of the joint. Each of these features diminishes or substantially eliminates any stress transmitted to the interface between each of stems 19 and 36 and its respective medulla, thereby assuring that the prosthesis will remain properly implanted at all times notwithstanding the freedom of movement of the finger relative to the MP joint.

During radial and ulnar deviation of the proximal phalanx 15 relative to head 17 when prosthesis 10 is in place, there can be and generally is a progressive extraction of part 48 from bore 34 in the volar extent of element 30. Also, hyperextension forces of the prosthesis allow the distal end of part 48 of pin 46 to move dorsally in slot 26, the width of portion 26b of slot 26 being slightly wider than the transverse dimension of part 48 of pin 46 as shown in FIG. 4.

While parts 48 and 50 of pin 46 have been shown to be at right angles to each other, they can be slightly (or moderately) greater or less than 90° from each other to minimize stress or wear at the interfaces of these parts with members 12 and 14. Pins 32 and 46 and member 12 will generally be metallic and member 14 and element 30 will generally be of plastic material so that there will be no metal-to-metal contact between adjacent parts; it is understood however that the prosthesis could be constructed of other materials such as ceramics. Also, the shape of pin 46 can be changed with reference to members 12 and 14. Specifically, part 48 of pin 46 is generally parallel to and above tunnel 54 of flexor tendons 56 of the finger when the prosthesis is in place. This allows also for a more volar placement of the junction of the two parts of pin 46 and diminishes the dorsal extent of the open section in the distal end of head 17 while increasing the amount of material available in the proximal end of member 14 for pin part 50 to be placed in.

The shape of head 17 of member 12 can be varied and might be different in shape for each of the fingers and thumb. In each instance, the essence of the shape and size will nearly reproduce the normal metacarpal head with its attached collateral ligaments as these ligaments are quite bulky and, collectively with the normal metacarpal head, give the finished semi-spherical shape to the same. Also, stem 19 of member 12 for the index finger will generally have a different angle than that for the long finger, and stem 19 of member 12 designed for the ring finger will be essentially straight without being angled. Specific angles for members 12 of the various prosthesis for the various fingers can be determined by measurements of specific hands. Also, element 30 should have its flexion-extension axis generally perpendicular to the longitudinal axis of the proximal phalanx, and the plane of element 30 should be generally perpendicular to the flexion-extension axis of the MP joint. Projection 33 of element 30 is provided to minimize the length of part 48 of pin 46 that is exposed to bending moments induced by the volar subluxating forces of the flexor tendons on the proximal phalanx.

Figure 11:
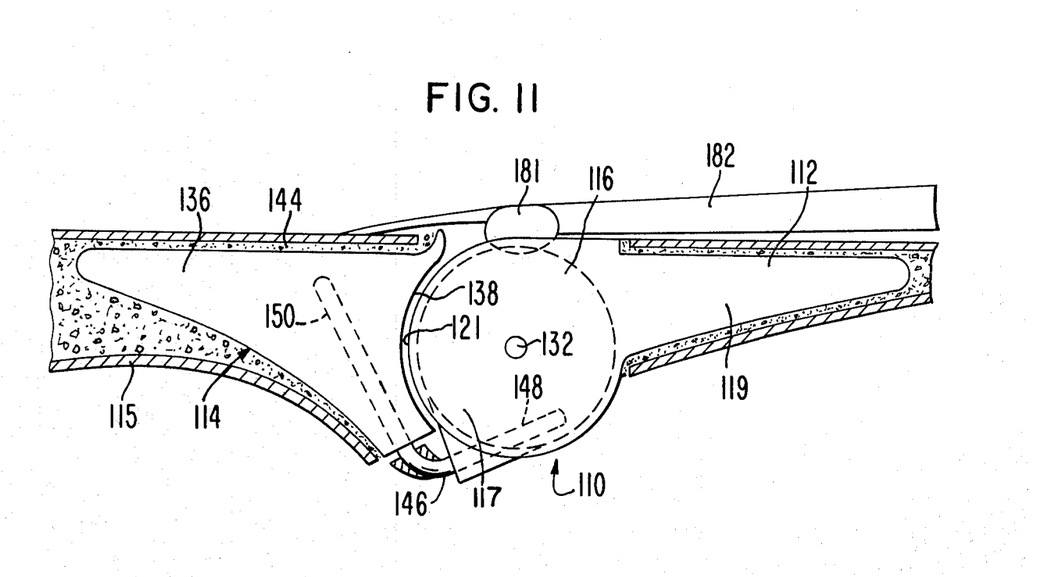
FIG. 11 is a view similar to FIG. 1 but showing an embodiment of the prosthesis used with the knee joint.

The adaption of the prosthesis of this invention for use in the knee joint is depicted in FIG. 11 which shows a side elevational view of the prosthesis 110. This prosthesis has stem members 119 and 136 with end faces 121 and 138, respectively, and a pivot mechanism comprised of a rotatable element 130 coupled by a pin or shaft 132 to the head 116 at one end of member 119. An L-shaped pin 146 having parts 148 and 150 pivotally interconnects member 136 with element 130 in the same manner as described above with respect to prosthesis 10.

Figure 11A:
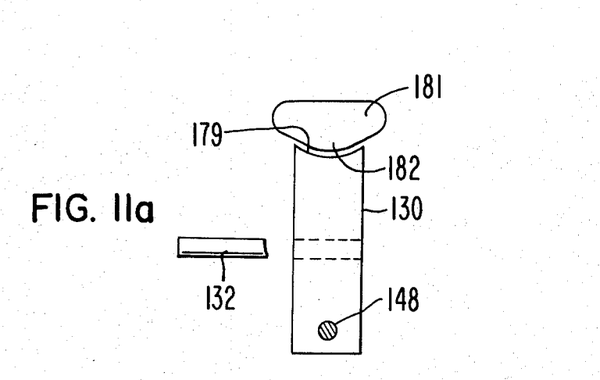
FIG. 11a is an end elevational view of the rotatable element of the prosthesis of FIG. 11, showing the way in which the patella is coupled therewith.

Element 130 is of similar height to the prosthetic femoral condyles 117 in such a manner that the periphery of a disc-like version of element 130 presents itself anteriorly so that it can have a groove 179 to accept the deep surface 182 of the patella 181 as seen in FIG. 11a. During flexion and extension of the knee, the patella rides in groove 179 or other suitable receptacle on the anterior surface of the generally disc-shaped element 130 in such a manner that it transfers the joint reaction force which normally occurs between the patella and the femoral condyles to the flexionextension axis pin 132. Groove 179 thereby reconstructs the patello-femoral joint of the knee. In addition, part 148 of pin 146 reconstructs the longitudinal rotational axis of the knee joint in a manner analogous to the way part 48 of pin 46 reconstructs the longitudinal rotational axis of the MP joint. The x and y distances shown in FIG. 11 are substantially equal to each other in constrast to the corresponding distances for prosthesis 10. As in the concept of the present invention for the MP joint of the hand, the ability of the pivot mechanism to dissipate torsional and bending moments from the prosthesis and its interface with the bone assures the continued successful implantation of the same.

While the invention as described in FIGS. 1-4 is applied to the MP joint of the human hand and in FIG. 11 is applied to the knee, it is understood that the knee version is suitable for application to the MP joint of the finger and that, in such a case, rotatable element 130 which is shown in FIG. 11 as being notched on its anterior aspect to receive the deep aspect 182 of the patella 181 would also serve to receive the extensor tendon to the finger at the level of the MP joint, thereby serving to help stabilize and centralize the extensor tendon over the dorsal aspect of the MP joint. Similarily, the present invention as shown in FIGS. 1-4 for use in the MP joint of the finger is also suitable for prosthetic replacement of the knee joint, under which circumstances surface 25 of stem member 12 is grooved which groove extends from surface 25 onto surface 21, thereby notching the dorsal and distal surface of the same to receive the generally pointed and convex deep surface 182 of the patella.

Figure 12:
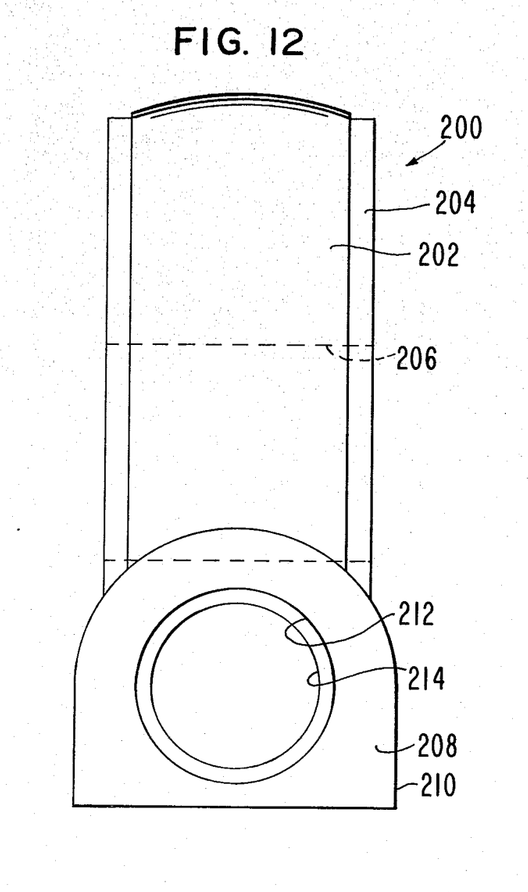
Figure 13:
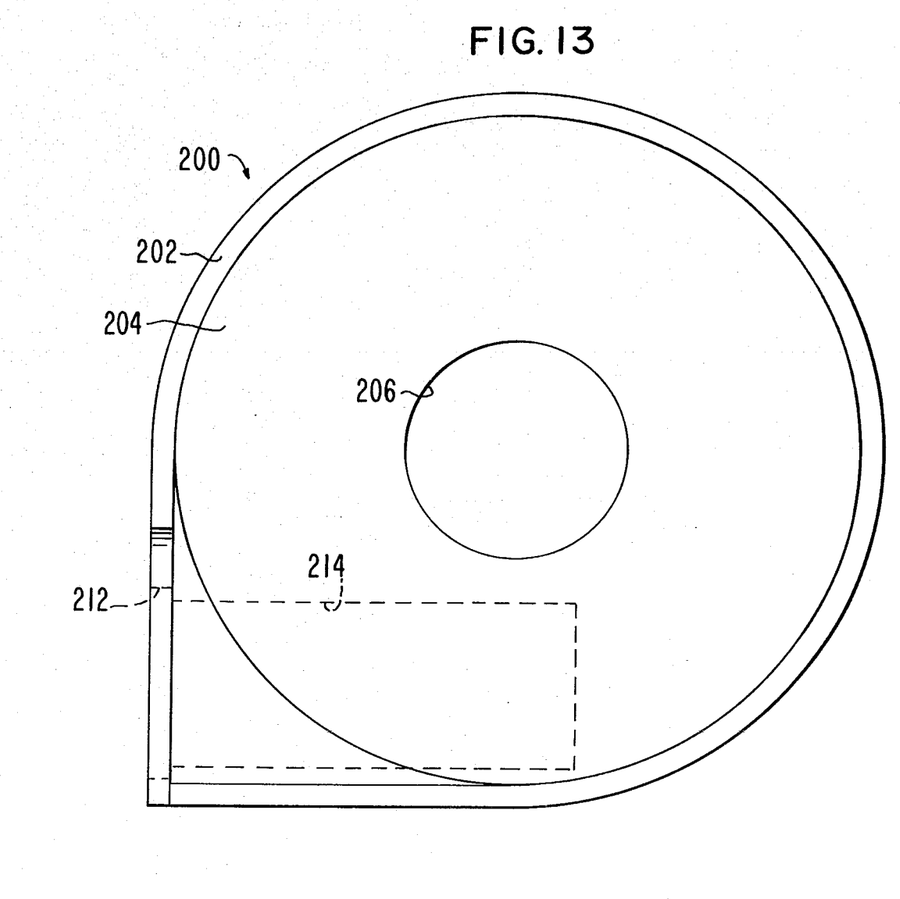
FIG. 13 is a side elevational view of the disk of FIG. 12.

An improved rotatable element 200 (FIGS. 12 and 13) for use with head 17 instead of element 30 is shown in FIGS. 12 and 13. It includes a metallic band 202 which encircles a plastic body 204 having a central hole 206 therethrough. Band 202 has a flat face 208 defining a flange 210 surrounding an opening 212 which is aligned with a bore 214 extending into plastic body 204. Opening 212 is of slightly larger diameter than bore 214.

The purpose of flange 210 is to permit an increase in the diameter of part 48 of pin 46 and thereby an increase in the strength of the pin. Flange 210 extends from the surface of the spherical metacarpal head and, because the flange is wider than body 204, the flange will allow for transmission of tension forces about the periphery of band 202 which will continue to snap onto body 204. The body 204 projects laterally from opposed sides of band 202 in the manner shown in FIG. 12.

Figure 14:
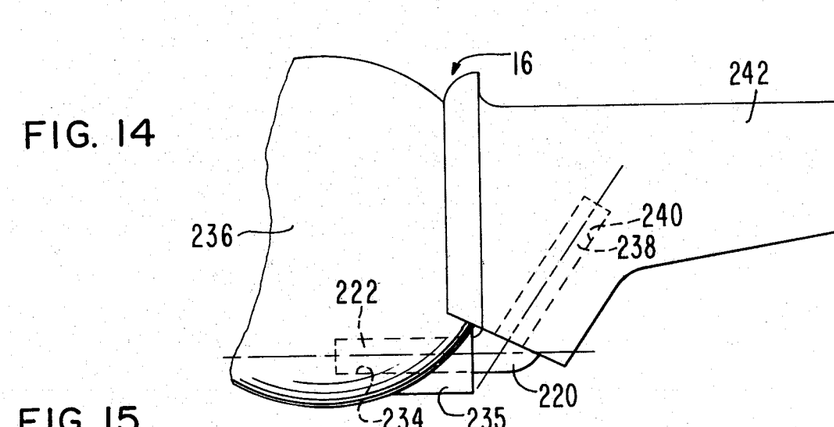

FIG. 14 shows an improvement in the pivot pin forming part of pivot mechanism 16. As shown in FIG. 14, pin 220 includes a first part 222 rotatably and slideably received within the bore 234 in the rotatable element 235 in metacarpal head 236. The second part 238 of pin 220 is rotatably and slideably received within a bore 240 in a phalangeal member 242. The angle between parts 238 and 222 of pin 220 is shown in FIG. 14 as being greater than 90°. It can be less than 90° and range up to as much as 125° or above. A number of benefits accrue from the use of an obtuse angle on pin 220. These include decreased bending moments on the pin and bringing the disk in head 236 into more extension to allow for greater disk flexion before the protuberance of the disk runs into the junction of the head with the stem on the volar side of the joint.

Figure 15:
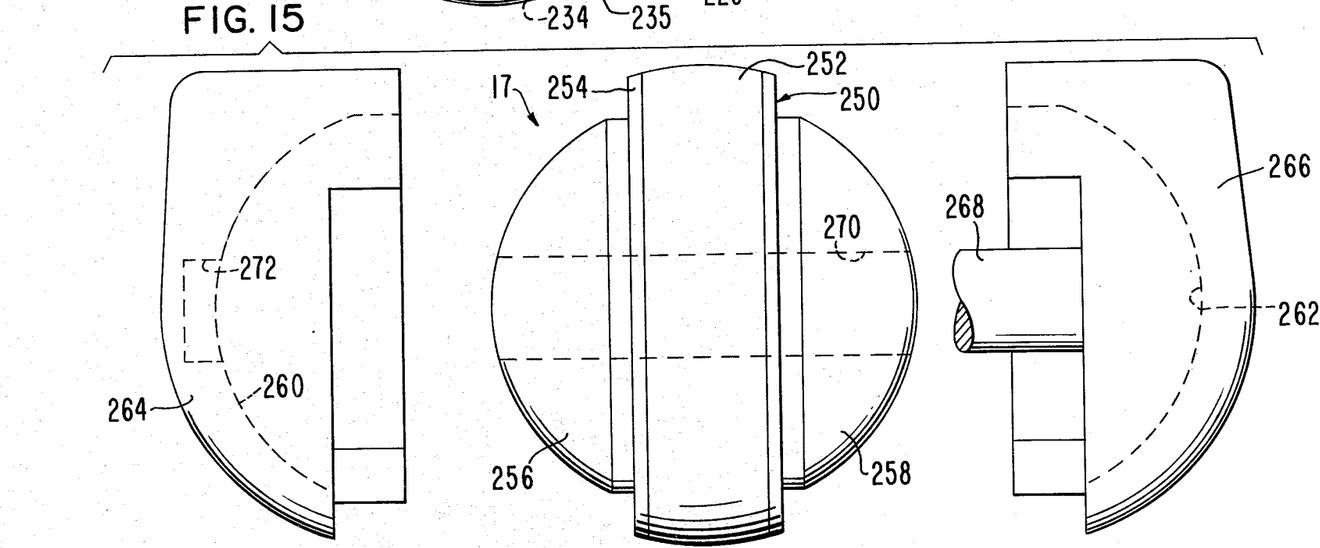
FIG. 15 is an exploded view of the metacarpal head forming the melacarpophalangeal joint of the prosthesis of the present invention.

An improvement of head 17 is shown in FIG. 15 and includes a rotatable element 250 having a metal band 252 surrounding a plastic central body 254 similar to the rotatable element 200 shown in FIGS. 12 and 13.

Element 250 has a pair of generally spherical halves 256 and 258 which project laterally from body 254 and are secured thereto in any suitable manner. Halves 256 and 258 are rotatably received within spherical recesses 260 and 262 in side members 264 and 266, respectively.

Member 266 has a shaft 268 which passes through a central bore 270 extending through element 250 and entering a recess 272 extending into recess 260. Shaft 268 is releaseably secured in any suitable manner in recess 272 to interconnect members 264 and 266 yet allow element 250 to rotate relative to members 264 and 266 within recesses 260 and 262.

FIG. 15 shows the radial and ulnar halves of an improved metacarpal head from a distal or end-on view; thus, the stem or member comparable to member 12 for insertion into the metacarpal bone of a thumb or finger is not shown in FIG. 15, such member 12 having respective portions secured to the radial and ulnar halves of the head.

The reason that element 250 is generally spherical is that the additional plastic of element 250 will fit into the concave recesses 260 and 262 of members 264 and 266 which are on the radial and ulnar sides, respectively of the metacarpal head. Also, the increase in diameter of the pin as described above with respect to FIGS. 12 and 13 will necessitate the increase in the mass of plastic on body 254 surrounded by band 252 (FIG. 15). Also, some benefit is obtainable from a larger bearing surface once significant wear occurs between the shaft 268 and spherical halves 256 and 258. In element 250, band 252 snaps onto body 254 and is held thereon by the snap fit.

Figure 16:
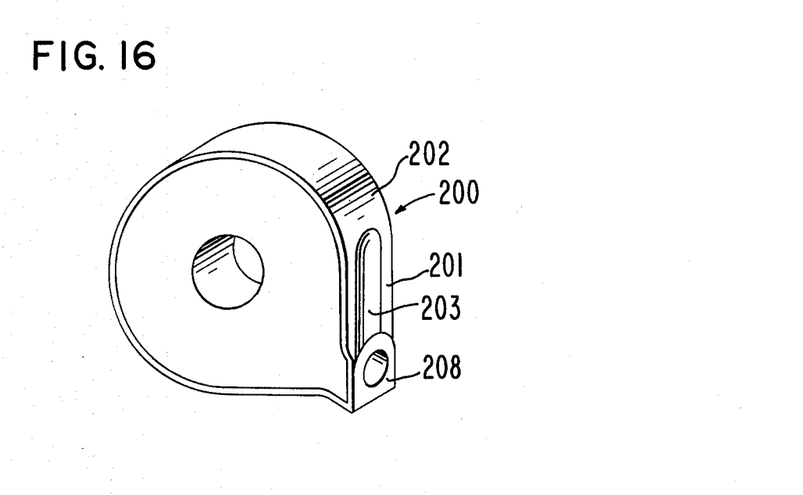
FIG. 16 is a perspective view of the disk in FIG. 12 with an improved front face therein.
Figure 17:
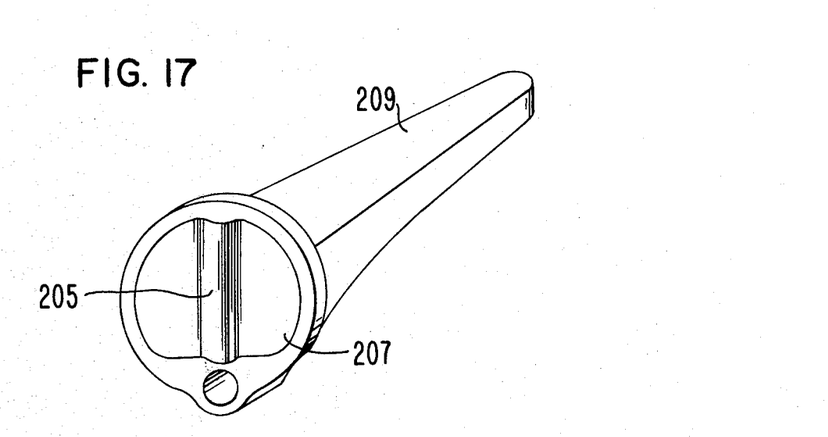
FIG. 17 is a perspective view of the phalanegeal portion of the prosthesis of this invention.
Figure 18:
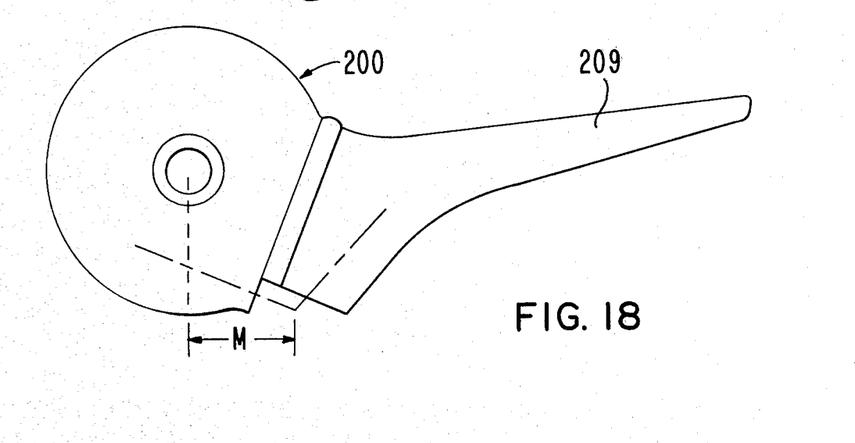
FIG. 18 is a side elevational view of the prosthesis with the parts of FIGS. 16 and 17 coupled together.

An improvement in the rotatable element 200 shown in FIGS. 12 and 13 is shown in FIG. 16. In this view, the flat face 201 has a concave groove 203 therein above flange 208. This concave groove is elongated and extends partially along the outer periphery of band 200 adjacent to the base 207 of phalangeal portion 209. Groove 203 is adapted to receive a convex protuberance 205 at base 207 of the phalangeal portion 209. If a substantially flat interface is achieved between a portion of element 200 and the base 207 as shown in FIG. 18, volar subluxing forces on the base of the proximal phalanx will be converted substantially into shear forces on the longitudinal limb of the pin pivotally interconnecting element 200 with member 209 at the point where the pin exits from element 200. In FIGS. 16 and 17, volar subluxing forces on base 207 tend to rotate element 200 and thereby exert a large bending moment (labeled M in FIG. 18) on the pin. Such a large bending moment is present only when a circular disk meets a similar concavity in the phalangeal part of the joint. When their interface is flat against a portion of the periphery of element 200, the bending moment is substantially eliminated.

What is claimed is:

1. A prosthesis for a joint of the human body with the joint being at the junction of a pair of normally aligned bones comprising: first and second elongated members, the first member adapted to be inserted into one of the bones adjacent to the joint and the second member adapted to be inserted into the other bone adjacent to the joint, the members having respective ends adjacent to each other when the same are inserted into respective bones; and means pivotally interconnecting the adjacent ends of said members, said means including a first element carried by one of the members for rotation relative thereto about a first axis, and a second element having a pair of relatively angularly disposed parts shiftably coupled with said first element and said second member, respectively, for rotation relative thereto about second and third axes, respectively, whereby said second member can pivot relative to the first member about any one of said axes without imparting substantial torsional and bending loads to the first member.

2. A prosthesis as set forth in claim 1, wherein the angle between the parts of the second element is greater than 90°.

3. A prosthesis as set forth in claim 1, wherein said second element is a generally L-shaped pin.

4. A prosthesis as set forth in claim 1, wherein said first element has a first bore spaced from the first axis, one of the parts of said second element being rotatably and slidably received in said first bore.

5. A prosthesis as set forth in claim 4, wherein the other member has a second bore therein, the other of said parts of the second element being rotatably and slidably received in said second bore.

6. A prosthesis as set forth in claim 1, wherein the adjacent end of said first member has a slot therein, said first element being in the slot, a shaft rotatably mounting said first element for rotation relative to said first member about said first axis, said second element including a pin pivotally connecting the first element with said second member to permit the second member to rotate relative to the first element about said second and third axes.

7. A prosthesis as set forth in claim 6, wherein said pin is generally L-shaped to present a pair of angularly disposed parts, said element having a first bore for rotatably receiving one of the parts, said second member having a second bore for rotatably receiving the other part.

8. A prosthesis as set forth in claim 7, wherein the first bore is radially spaced from said shaft, said second bore being near the adjacent end of said second member and at an angle relative to the longitudinal axis of the second member.

9. A prosthesis as set forth in claim 7, wherein said parts of said pin are removably received in respective bores.

10. A prosthesis as set forth in claim 7, wherein the pin has a shoulder on the other part near its junction with said one part, said shoulder defining a bearing surface engageable with said second member.

11. A prosthesis as set forth in claim 6, wherein the first member has a generally spherical outer face at said adjacent end thereof, the slot extending into said first member near the lower portion thereof, the slot having an opening at said outer face.

12. A prosthesis as set forth in claim 11, wherein the distance between the shaft to the opening of the slot is less than the distance from the shaft to a location on the member diametrically opposite to said slot opening.

13. A prosthesis as set forth in claim 11, wherein the distance between the shaft to the opening of the slot is substantially equal to the distance from the shaft to a location on the member diametrically opposite to said slot opening.

14. A prosthesis as set forth in claim 6, wherein said first member has an upper surface provided with a groove therein, the groove extending to said adjacent end of the first member.

15. A prosthesis as set forth in claim 6, wherein the slot extends from the upper part of the first member to the lower part thereof, said element having an outer peripheral groove therein near the upper part of the slot.

16. A prosthesis as set forth in claim 6, wherein said first member has a pair of opposed sides, the slot being centrally disposed between the sides, the element having a generally circular outer periphery, the first bore being adjacent to said outer periphery.

17. A prosthesis as set forth in claim 1, wherein said first member has a convex face at said adjacent end thereof, said second member having a surface substantially complemental to said convex face at said adjacent end of the second member.

18. A prosthesis for a joint of a human body with the joint being at the junction of a pair of normally aligned bones which can move relative to each other comprising: first and second elongated members, there being a member for each bone at the joint, respectively, each member having a stem adapted to be inserted into the respective bone and an end portion projecting outwardly from the bone when the stem is inserted therein, the end portion of the first member having a generally spherical outer surface and the end portion of the other member having a surface substantially complemental to at least a portion of the spherical surface of the first member, the end portion of said first member having a pair of opposed sides and a slot extending thereinto between the sides from said outer surface thereof; a rotatable element in the slot; a shaft carried by the sides of the end portion of the first member and coupled with the element for mounting the latter on the first member for rotation about the axis of the shaft, the element having an outer periphery adjacent to said outer surface of the end portion of the first member, said element having a first bore extending thereinto from the outer periphery thereof, the first bore being radially spaced from the shaft and being generally parallel with a diametral line passing through the shaft, the second member having a second bore extending into the end portion thereof; and an L-shaped pin having first and second elongated parts rotatably and slidably receivable in the first and second bores, respectively, the element, the shaft and the pin defining a pivot mechanism permitting movement of the second member relative to the first member about the longitudinal axes of the shaft, the first part and the second part without imparting torsional and bending loads to the first member.

19. A prosthesis as set forth in claim 18, wherein the second bore is at an acute angle relative to the longitudinal axes of the second member.

20. A prosthesis as set forth in claim 18, wherein the second part of the pin has a shoulder near the junction between the first and second parts, the shoulder defining a bearing surface engageable with the second member.

21. A prosthesis as set forth in claim 18, wherein the end portion of the first member has a dorsal extremity and a volar extremity, the distance between the shaft and the dorsal extremity being greater than the distance between the shaft and the volar extremity.

22. A prosthesis for a joint of the human body with the joint being at the junction of a pair of normally aligned bones comprising: first and second elongated members, the first member adapted to be coupled to one of the bones adjacent to the joint and the second member adapted to be coupled to the other bone adjacent to the joint, the members having respective ends externally of said bones and in substantial juxtaposition to each other when the members are inserted into respective bones; and means pivotally interconnecting said members to permit said second member to pivot relative to the first member about any one of three relatively angularly disposed axes as said respective ends remain in substantial juxtaposition to each other and without imparting substantial torsional and bending loads to the first member, the adjacent end of the second member being normally movable along said adjacent end of the first member for predetermined rotational displacements of the second member about said axes relative to the first member, the adjacent end of the second member being movable away from the adjacent end of the first member when the rotational displacement of the second member about at least a first of the axes relative to the first member is greater than the corresponding predetermined displacement, whereby an excessive load can be exerted on the second member without damaging the pivotal connection between the first and second members and without impairing the coupling between each of said members and the respective bones.

23. A prosthesis for a joint of the human body with the joint being at the junction of a pair of normally aligned bones comprising: first and second elongated members, the first member adapted to be coupled to one of the bones adjacent to the joint and the second member adapted to be coupled to the other bone adjacent to the joint, the members having respective ends adjacent to each other when the same are inserted into respective bones; and means pivotally interconnecting the adjacent ends of said members to permit said second member to pivot relative to the first member about any one of three relatively angularly disposed axes without imparting substantial torsional and bending loads to the first member, the adjacent end of the second member being normally movable along said adjacent end of the first member for predetermined rotational displacements of the second member about said axes relative to the first member, said interconnecting means including a first element having a pair of relatively angularly disposed, elongated parts, a first of the parts being mounted on the first member for rotation about one of the axes and the second part being rotatably mounted on the second member for rotation about another of said axes, at least one of the parts being axially shiftable relative to the respective member to permit the adjacent end of the second member being movable away from the adjacent end of the first member when the rotational displacement of the second member about at least a first of the axes relative to the first member is greater than the corresponding predetermined displacement, whereby an excessive load can be exerted on the second member without damaging the pivotal connection between the first and second members and without impairing the coupling between each of said members and the respective bones.

24. A prosthesis as set forth in claim 23, wherein the first member has a second element rotatably mounted thereon for rotation about the third of said axes, said second element having a bore, said first part of the first element being rotatably and slidably received in the bore of the second element.

25. A prosthesis as set forth in claim 24, wherein the first member has a slot therein, said second element having a disk-like configuration, the second element being in the slot, a shaft rotatably mounting the second element on said first member, the second element have a bore therein, said first element being an L-shaped pin having a first, elongated part pivotally and slidably received in the bore of the second element, the second member having a second bore, the pin having a second, elongated part pivotally and slidably received in the second bore.

26. A prosthesis as set forth in claim 23, wherein the first element is a generally L-shaped pin.

27. A prosthesis as set forth in claim 23, wherein the angle between the parts of the first element is less than 90°.

28. A prosthesis as set forth in claim 23, wherein the angle between the parts of the first element is greater than 90°.

29. A prosthesis for a joint of the human body with the joint being at the junction of a pair of normally aligned bones comprising: first and second elongated members, the first member adapted to be inserted into one of the bones adjacent to the joint and the second member adapted to be inserted into the other bone adjacent to the joint, the members having respective ends adjacent to each other when the same are inserted into respective bones; and a rotatable mechanism pivotally interconnecting the adjacent ends of said members, said mechanism including a first element carried by one of the members for rotation relative thereto about a first axis, and a second element having a pair of relatively angularly disposed parts shiftably coupled with said first element and said second member, respectively, for rotation relative thereto about second and third axes, respectively, the first element having a metal band and a plastic body within the band, the second element including a pin having said parts rigidly coupled thereto.

30. A prosthesis as set forth in claim 29, wherein the band has a flange thereon near said pin, the band having a hole therethrough and said plastic body having a bore aligned with the hole, one part of the pin being rotatably and shiftably received in the hole and the bore.

31. A prosthesis as set forth in claim 30, wherein the diameter of the hole is greater than that of the bore.

32. A prosthesis as set forth in claim 29, wherein the angle between the parts of the pin is approximately 90°.

33. A prosthesis as set forth in claim 29, wherein the angle between the parts of the pin is greater than 90°.

34. A prosthesis as set forth in claim 29, wherein the angle between the parts of the pin is approximately 125°.

35. A prosthesis as set forth in claim 29, wherein the angle between the part of the pin is less than 90°.

36. A prosthesis as set forth in claim 29, wherein said first element has a pair of spherical halves secured to and extending laterally from respective sides of said body, said mechanism further including a pair of hollow members for rotatably receiving the halves of said first element, and means coupled with the members for interconnecting the same.

37. A prosthesis as set forth in claim 36, wherein each member has a spherically shaped recess for rotatably receiving the respective half of said first element, one of the members having a shaft for rotatably mounting the first element thereon.

38. A prosthesis as set forth in claim 29, wherein said band of said first element has surface means thereon for preventing rotation of the first element relative to said second member.

39. A prosthesis as set forth in claim 38, wherein said surface means is a groove in said band, said second member having a protuberance thereon shiftably received within the groove.

40. A prosthesis as set forth in claim 39, wherein the groove extends along a portion of the outer periphery of the band near said pin.

* * * * *